United States Patent [19]

D'Jang

[11] Patent Number: 5,910,308
[45] Date of Patent: Jun. 8, 1999

[54] HERBAL EXTRACT COMPOSITION CONTAINING *GYNOSTEMMA PENTAPHYLLUM, CRATAEGUS PINNATIFIDA* AND *CAMELLIA SINENSIS*

[75] Inventor: Arthur H. K. D'Jang, Collins, N.Y.

[73] Assignee: Sante International Inc., Jamestown, N.Y.

[21] Appl. No.: 08/905,128

[22] Filed: Aug. 1, 1997

Related U.S. Application Data

[60] Provisional application No. 60/042,540, Mar. 19, 1997.
[51] Int. Cl.$^6$ .............................. A61K 35/78; A61K 9/20; A61K 9/14; A61K 9/68
[52] U.S. Cl. ....................... 424/195.1; 424/464; 424/485; 424/48
[58] Field of Search ................................. 424/195.1, 464, 424/485, 48

[56] References Cited

U.S. PATENT DOCUMENTS

| | | | |
|---|---|---|---|
| 4,460,488 | 7/1984 | Grollier et al. | 426/330.3 |
| 4,698,360 | 10/1987 | Masquelier | 514/456 |
| 4,753,805 | 6/1988 | Cherukuri et al. | 426/5 |
| 4,935,256 | 6/1990 | Tsai | 510/119 |

FOREIGN PATENT DOCUMENTS 1105522  7/1995  China .

OTHER PUBLICATIONS

Remington' Pharmaceutical Sciences, 16th Edition, Mack Publishing Company, Easton, PA, pp. 1518–1523 and 1553–1557, 1980.

*Primary Examiner*—Michael G. Wityshyn
*Assistant Examiner*—Janet M. Kerr
*Attorney, Agent, or Firm*—Hodgson, Russ, Andrews, Woods & Goodyear, LLP

[57] ABSTRACT

Provided is an herbal extract-based composition comprising an extract of Gynostemma pentaphyllum, an extract of Crataegus pinnatifida (hawthorn leaves or berries), and an extract of Camellia sinensis (green tea). Also provided is a process for preparing a herbal extract-based composition which comprises separately extracting each of hawthorn berries, green tea leaves, and Gynostemma pentaphyllum leaves; drying extraction eluates obtained from the extracting of each of hawthorn berries, green tea leaves, and Gynostemma pentaphyllum leaves to obtain organic residues in forming a hawthorn berry extract powder, green tea extract powder, and a Gynostemma pentaphyllum extract powder; and combining the green tea extract powder, the Gynostemma pentaphyllum extract powder, and the hawthorn berry extract powder in desired proportions to form the herbal extract-based composition which has health promoting effects including potent inhibition of free radicals.

20 Claims, No Drawings

HERBAL EXTRACT COMPOSITION CONTAINING GYNOSTEMMA PENTAPHYLLUM, CRATAEGUS PINNATIFIDA AND CAMELLIA SINENSIS

This is a nonprovisional application based on my earlier copending provisional application Ser. No. 60/042,540 filed on Mar. 19, 1997, the disclosure of which is herein incorporated by reference.

FIELD OF THE INVENTION

The present invention relates to an herbal extract-based composition comprised of a combination of three components: an extract of *Gynostemma pentaphyllum,* an extract of *Crataegus pinnatifida,* and an extract of *Camellia sinensis.* The present invention also provides a method of making the composition for therapeutic uses, and as a dietary supplement for promoting health.

BACKGROUND OF THE INVENTION

Generally, herbal supplements are natural, safe when taken as recommended, and less expensive and sometimes more effective alternatives to drugs. These plant-based pharmaceuticals are used for medicinal purposes; and/or dietary supplements for disease prevention, for relief of ailments, and for health maintenance (collectively "health-promoting"). *Gynostemma pentaphyllum, Crataegus pinnatifida,* and *Camellia sinensis* have been used individually for particular therapeutic applications.

1. *Gynostemma pentaphyllum*

*Gynostemma pentaphyllum,* also known as 5-leaf ginseng or jiaogulan or southern ginseng, is from the cucumber family and has traditionally been grown in a mountainous region in South Central China. This herb, a completely different plant than ginseng, is rich in special saponins termed "gypenosides" which are similar, and some identical, to the ginsenosides found in ginseng, but at a level several fold higher. These saponins have been shown to have antioxidant/cell protective effects. More particularly, the saponins protected cell membranes and cytosols, from oxidative injury, neutralize free radicals, helped preserve immune function during irradiation, lowered blood pressure, reduced vascular resistance, effects anti-platelet-aggregation, and reduced levels of serum triglycerides and total cholesterol (Gormley et al., 1997, *Better Nutrition* 59:42).

2. *Crataegus pinnatifida*

The leaves and berries of *Crataegus pinnatifidia,* also known as hawthorn, have been used traditionally for the treatment of heart conditions and for cardiovascular health. The hawthorn fruits (berries), known as "Shan-zha", have been used to improve digestion, and to alleviate various stomach ailments. Saponins, flavonoids (including hyperoside), and anthocyanins (including proanthocyanidins) extracted form hawthorn fruits have also shown cardiotonic (heart stimulating and regulating) activity including inhibition of arrhythmia, normalization of blood pressure, dilation of blood vessels and increase in coronary blood flow, reduction of serum triglyceride and cholesterol levels, reduction in symptoms of angina, and improvement of circulation (Foster, 1997, *Better Nutrition,* 59:56; Foster, 1989, *Bestways* 17:46; McCaleb, 1991, *Better Nutrition for Today's Living* 53:32).

3. *Camellia sinensis*

Dried leaves from the *Camellia sinensis* plant is processed into three types of tea: oolong tea, black tea, and green tea. In making green tea, the tea leaves are stabilized by moist or dry heat which destroys the enzyme polyphenoloxidase and thus, prevents oxidation of polyphenols. These polyphenols are the main biologically active ingredients in green tea. Catechins, a chemical group of polyphenols possessing antioxidant properties (protects cells from free radical-mediated damage), include epigallocatechin-3 gallate (ECGC), epigallocatechin, and epicatechin-3-gallate. Recently, ECGC has been shown to be an inhibitor of urokinase, and enzyme crucial for cancer growth (Jankun et al., 1997, *Nature* 387:561). The polyphenols in green tea, accounting for as much as 40% of tea's dry solids, have also been shown to reduce serum cholesterol and LDL (low density lipoprotein). Green tea polyphenols have been shown to prevent microbial (bacterial and viral) infections. For example, green tea polyphenols damage bacterial membranes (Dolby, 1997, *Better Nutrition,* 59:22). Further, extracts of green tea have been shown to prevent cancers of the lung, breast, prostate, liver, skin, esophagus, and colon. Green tea is also high in cavity-fighting fluoride—the amount of tea used to prepare one cup has approximately 0.3 milligrams of fluoride.

While *Gynostemma pentaphyllum, Crataegus pinnatifida,* and *Camellia sinensis* have been used individually for health promoting and therapeutic purposes, not described is the arrangement and composition comprising an extract of *Gynostemma pentaphyllum,* an extract of *Crataegus pinnatifida* (hawthorn berries or leaves) and an extract of *Camellia sinensis* (green tea) for health promoting and therapeutic uses.

SUMMARY OF THE INVENTION

This invention relates to a herbal extract-based composition that comprises about 10 to about 30 percent by weight of *Gynostemma pentaphyllum* extract, about 10 to about 30 percent by weight of green tea extract, and about 40 to about 75 percent by weight of hawthorn berries extract. Preferably, the herbal extract-based composition comprises about 20 percent by weight of *Gynostemma pentaphyllum* extract, about 20 percent by weight of green tea extract, and about 60 percent by weight of hawthorn berries extract.

Another aspect of the present invention is a process for preparing the herbal extract-based composition. Essentially, this method comprises separately extracting each herbal component (hawthorn berries, green tea leaves, and leaves of *Gynostemma pentaphyllum*); drying the extraction eluates to obtain the organic residues in forming a hawthorn berry extract powder, green tea extract powder, and a *Gynostemma pentaphyllum* extract powder; and combining the green tea extract powder, the *Gynostemma pentaphyllum* extract powder, and the hawthorn berry extract powder in desired proportions to form the herbal extract-based composition. In one embodiment, this method comprises the steps of:

(a) separately extracting a first batch of macerated hawthorn berries, cut green tea leaves, and cut *Gynostemma pentaphyllum* leaves in warm (greater than room temperature) water;

(b) recovering a first extract eluate from the respective extraction of each herbal component;

(c) repeating step (a), recovering a second extract eluate and pooling the first and second extract eluates of the respective herbal component;

(d) separately extract a second batch of macerated hawthorn berries, cut green tea leaves, and cut *Gynostemma pentaphyllum* leaves in an aqueous alcohol (e.g., 70% ethanol);

(e) recovering a first aqueous alcohol extract eluate from the respective aqueous alcohol extraction of each herbal component;

(f) repeating step (d), recovering a second aqueous alcohol extract eluate from the respective aqueous alcohol extraction of each herbal component, and pooling the second aqueous alcohol extract eluate with the respective first aqueous alcohol extract eluate from each herbal component;

(g) recovering the organic residue of each herbal component by reducing the liquid portion of each of the respective pooled eluates by drying (air drying, freeze drying or a combination thereof), in forming a green tea extract powder, a *Gynostemma pentaphyllum* extract powder, and a hawthorn berry extract powder;

(h) combining the green tea extract powder, the *Gynostemma pentaphyllum* extract powder, and the hawthorn berry extract powder in the desired proportions. It is noted that the pooled water extract eluate and the pooled aqueous alcohol extract eluate from each herbal component were dried separately and then the organic residues for that herbal component combined to form the extract powder for that herbal component; or alternatively, the pooled water extract eluate and the pooled aqueous alcohol extract eluate from each herbal component may be combined and then dried to form the extract powder for that herbal component.

DETAILED DESCRIPTION OF THE INVENTION

The present invention relates to a novel herbal extract-based composition that comprises about 10 to about 30 percent by weight of *Gynostemma pentaphyllum* extract, about 10 to about 30 percent by weight of green tea extract, and about 40 to about 75 percent by weight of hawthorn berries extract. Preferably, the herbal extract-based composition comprises about 20 percent by weight of *Gynostemma pentaphyllum* extract, about 20 percent by weight of green tea extract, and about 60 percent by weight of hawthorn berries extract. *Gynostemma pentaphyllum, Crataegus pinnatifida,* and *Camellia sinensis* have been used individually for health promoting and therapeutic purposes. However, the herbal extract-based composition of the present invention is an arrangement and unique combination that has been found to provide previously unknown therapeutic or health promoting benefits. More particularly, the herbal extract-base composition, in a pharmacologically effective amount and regimen, can reduce the effects of aging such as the formation of brown spots; increases metabolism for elimination of lactate; reduces body weight, increases alertness; improves oxygen uptake for physical and mental performance; increases physical endurance; increases tolerance of oxygen deprivation; rejuvenates skin; reduces alcohol induced liver injury; improves red cell deformability; reduces plasma fibrinogen; inhibits thrombus formation; relieves constipation; reduces halitosis; inhibits oxidation of unsaturated fatty acids thereby suppressing undesirable body odor; helps to prevent the formation of cataracts; helps to prevent hyperglycemia; inhibits the breakdown of collagen by free radicals (thereby decreasing the manifestations of autoimmune diseases such as rheumatoid arthritis, scleroderma, and other collagen diseases); aids to detoxify the body from heavy metals (because of the ability of the composition to absorb and precipitate lead, mercury, nickel, chromium, silver and copper ions); aids to detoxify the body from alcohol (because of the ability of the composition to combine with alkaloids and act to neutralize toxicity and accelerate the elimination of alcohol through the urinary and gastrointestinal systems); aids to prevent formation, and to reduce the size if formed, of gallstones and lithiasis from the urinary tract; aids to inhibit or reduce prostate cancer cell growth and prostate hyperplasia; reduces reperfusion injury (by neutralizing free radicals and by lessening calcium accumulation in the myocardium and reducing plasma lactate dehydrogenase and creatine phosphokinase levels); aids to reverse memory impairment caused by drugs (e.g., alcohol, pentobarbital), reduces the frequency and severity of cerebral transient ischemia attacks, and shows a broader spectrum of antimicrobial activity than reported for green tea alone. Additional health promoting benefits that have been previously described as intrinsic to the separate components of the combination, and thus to the combination itself, include the benefits of inhibiting platelet aggregation; inhibiting the formation of dental plaque by inhibiting the growth of *Streptococcus mutans* (implicated in the formation of dental caries); and aiding in reducing the onset of certain forms of cancer, atherosclerotic heart disease, diabetes, and hypertension.

Depending on the desired use of the herbal extract-based composition according to the present invention to provide one or more particular health promoting and/or therapeutic effects, the composition can be provided as the main pharmacologically active components in a form including, but not limited to, a tea, a liquid extract, a beverage, a gum, a lozenge, a tablet (including capsule), or a topical agent. In one embodiment, the composition is included in a chewing gum formulation. The composition of chewing gum is conventional, and well known to those skilled in the art. For example, a gum base that may be mixed with the composition includes a base comprised of arabic, guar, natural rubber gums; sweeteners (sugar, stevia, saccharin, sorbitol, aspartame); flavoring agents (e.g., mints, fruits), coloring agents; or a combination thereof. In another embodiment, the composition is used as a tea.

In another embodiment, the composition is included in a beverage formulation. The composition of beverages are conventional, and well known to those skilled in the art. For example, an aqueous carrier that may be mixed with the composition includes carriers comprised of spring water, filtered water, distilled water, carbonated water, juices, or combinations thereof. Additionally, the beverage may further comprise components known to the beverage industry including preservative agents, sweeteners, flavoring agents, coloring agents, and combinations thereof.

In another embodiment, the composition is in extract form. The composition of herbal extracts are conventional, and well known to those skilled in the art. For example, an aqueous carrier that may be mixed with the composition includes carriers comprised of spring water, filtered water, or distilled water. Additionally, the extract may further comprise components including preservative agents, sweeteners, flavoring agents, coloring agents, and combinations thereof.

In another embodiment, where topical application to the skin or mucous membranes is desired to provide health promoting effects, the composition may be incorporated into a cream or ointment base. Suitable bases are known to those skilled in the art to include one or more of purified water, lanolin, propylene glycol, mineral oil, vegetable or flower oils, glycerin, glyceryl stearate, cetyl alcohol, propylparaben, preservatives, fragrance and the like. Formulations containing the herbal extract-based composition according to the present invention may comprise topical agents including, but not limited, to a rinse, a cream, an ointment, a gel, and a suppository. It will be appreciated by those skilled in the art that the pharmacological effective concentration of the herbal extract-based composition in the formulation will depend on other ingredients in the formulation, the mode of administration of the formulation, the physiologic site to be treated, and the desired health promoting or therapeutic effect to be provided.

In another embodiment, the composition may be incorporated into a tablet (including capsule, caplet, and the like). Suitable bases are known to those skilled in the art to include fillers, binders, coatings, excipients and combinations thereof. For example, base ingredients include, but are not limited to, plant cellulose, natural silica, magnesium stearate, wax, vegetable glycerides, vegetable stearate, and a combination thereof.

The therapeutic and/or health promoting benefits provided by the arrangement and unique combination of *Gynostemma pentaphyllum* extract, green tea extract, and hawthorn berries extract comprising the herbal extract-based composition of the present invention may be more apparent by the following examples which are provided for purposes of illustration, and not limitation.

EXAMPLE 1

In this embodiment is illustrated a process for preparing the herbal based-extract of the present invention. In this process of preparation, selectively extracted from each component herb are compounds (some yet to be chemically defined) with particular types of pharmacological activities. Using this process results in extracts that contain high concentrations of pharmacologically active compounds which comprise the active ingredients in the herbal extract-based composition of the present invention. The extraction process of the present invention selectively extracts target compounds of desired pharmacological activity, and thus, the extraction process should not be considered a "traditional extraction"; and the resultant extract is more appropriately viewed as a selective concentration of a combination of pharmacologically active components rather than a "total extract". Thus, using the method according to the present invention is an approach to control the quality of, and standardize the composition of the target compounds to be selectively extracted for, the herbal extract-based composition of the present invention.

The method according to the present invention comprises separately extracting each of hawthorn berries (or leaves), green tea leaves, and *Gynostemma pentaphyllum*; drying extraction eluates obtained from the extracting of each of hawthorn berries, green tea leaves, and *Gynostemma pentaphyllum* leaves to obtain organic residues in forming a hawthorn berry extract powder, green tea extract powder, and a *Gynostemma pentaphyllum* extract powder; and combining the green tea extract powder, the *Gynostemma pentaphyllum* extract powder, and the hawthorn berry extract powder in desired proportions to form the herbal extract-based composition. In one embodiment of the present invention, the method comprises the steps of:

(a) separately extract a first batch of macerated hawthorn berries, cut green tea leaves, and cut *Gynostemma pentaphyllum* leaves ("the herbal components") in warm (greater than room temperature) water;

(b) recovering a first extraction eluate from the respective extraction of each herbal component;

(c) re-extracting each herbal component by repeating step (a), recovering a second extraction eluate, and pooling the second extraction eluate with the first extraction eluate of the respective herbal component;

(d) separately extracting a second batch of macerated hawthorn berries, cut green tea leaves, and cut *Gynostemma pentaphyllum* leaves in an aqueous alcohol (e.g., 70% ethanol);

(e) recovering a first aqueous alcohol extraction eluate from extracting the second batch of each herbal component;

(f) re-extracting the second batch of each herbal component by repeating step (d), recovering a second aqueous alcohol extraction eluate, and pooling the second aqueous alcohol extraction eluate with the first aqueous alcohol extraction eluate of the respective herbal component;

(g) recovering the organic residue from each of the pooled extraction eluates by reducing the liquid portion of each of the pooled extraction eluates by drying (air drying, freeze drying, or a combination thereof) in forming a green tea extract powder, a *Gynostemma pentaphyllum* extract powder, and a hawthorn berry powder;

(h) combining the green tea extract powder, the *Gynostemma pentaphyllum* extract powder, and the hawthorn berry extract powder in the desired proportions.

In a preferred embodiment, the process for making the herbal extract-based composition comprises the steps of:

(a) macerating hawthorn berries, and cutting the green tea leaves and cutting the *Gynostemma pentaphyllum* leaves into small pieces (e.g., millimeter size) while keeping the three components separate;

(b) placing the macerated hawthorn berries, cut green tea leaves, and cut *Gynostemma pentaphyllum* leaves ("the herbal components") into separate containers;

(c) separately diluting each herbal component in warm water, preferably at in a temperature range of between approximately 70° C. to 80° C., preferably in a ratio range of water to each herbal component of five to one;

(d) allowing each herbal component to soak in the warm water for at least 1 hour (preferably for 2–4 hours);

(e) collecting an extraction eluate from each soaking of the herbal components into separate receptacles;

(f) re-extracting the macerated hawthorn berries, cut green tea leaves, and cut *Gynostemma pentaphyllum* leaves in a warm solution of water by repeating steps (c)–(d);

(g) collecting a re-extraction eluate from each re-extraction of each of the herbal components and pooling the re-extraction eluate with the extraction eluate of the respective herbal component; and in an extraction of a second batch of macerated hawthorn berries, cut green tea leaves, and cut *Gynostemma pentaphyllum* leaves in an aqueous alcohol;

(h) placing the second batch of macerated hawthorn berries, cut green tea leaves, and cut *Gynostemma pentaphyllum* leaves ("the herbal components") into separate containers;

(i) separately diluting each herbal component in an aqueous alcohol solution (preferably, 70% ethanol; preferably at room temperature, e.g., a range of between approximately 25° C. to 40° C.; preferably in a ratio range of alcohol solution to each herbal component of five to one);

(j) allowing each herbal component to soak in the aqueous alcohol solution for at least 1 hour (preferably for 2–4 hours);

(k) collecting the aqueous alcohol solution extraction eluate from the soaking of each of the herbal components into separate receptacles;

(l) re-extracting the second batch of macerated hawthorn berries, cut green tea leaves, and cut *Gynostemma pentaphyllum* leaves in an aqueous alcohol solution by repeating steps (i)–(j);

(m) collecting the aqueous alcohol solution re-extraction eluates ha from the soaking of each of the herbal components and pooling each aqueous alcohol solution supernatant re-extract with the aqueous alcohol solution extraction eluate of the respective herbal component;

(n) recovering the organic residue from the pooled aqueous alcohol extraction eluate of each herbal component by reducing the liquid portion of each of the respective pooled aqueous alcohol extraction eluate by drying (air drying, freeze drying, or a combination thereof) in forming a green tea extract powder, a *Gynostemma pentaphyllum* extract powder, and a hawthorn berry extract powder; and (o) combining the green tea extract powder, the *Gynostemma pentaphyllum* extract powder, and the hawthorn berry extract powder in the desired proportions to form a herbal extract based composition.

In illustrating a preferred embodiment, and following the process for producing the herbal extract-based composition, the herbal extract-based composition may be formed by mixing about 10 to about 30 percent by weight of *Gynostemma pentaphyllum* extract powder, about 10 to about 30 percent by weight of green tea extract powder, and about 40 to about 75 percent by weight of hawthorn berries extract powder. In a more preferred embodiment, the herbal extract-based composition comprises about 20 percent by weight of *Gynostemma pentaphyllum* extract powder, about 20 percent by weight of green tea extract powder, and about 60 percent by weight of hawthorn berries extract powder. Continuing this illustration of a preferred embodiment, the herbal extract-based composition is formed into a caplet, wherein the *Gynostemma pentaphyllum* extract powder, green tea extract powder, hawthorn berries extract powder comprise 500 mg. In such caplet form, and intrinsic to the herbal extract-based composition is typically found at least 75 mg (or at least 15% by weight) of proanthocyanidins, at least 75 mg (or at least 15% by weight) saponins (e.g., gypenosides) and at least 75 mg (or at least 15% by weight) green tea polyphenols. In such caplet form, a preferred dosage and regimen for an adult male or female to effect the health promoting and/or therapeutic effects provided by the herbal extract-based composition of the present invention is 1 caplet, three times daily; and preferably shortly before meals.

EXAMPLE 2

In this embodiment is illustrated a use of the herbal extract-based composition of the present invention. In this illustration, 20 post-thrombotic stroke in-patients (mean age 59±6; 16 males, 4 females) with hemiparesis and/or focal neurological deficits of mild to moderate degree of severity took the caplet dosage and regimen illustrated above for a period of at least 30 days, in addition to any standard symptomatic therapy. After the 30 day period, patients taking the herbal extract-based composition, as compared to the control group of patients not taking the herbal extract-based composition, showed significant improvement. The significant improvement in the treated group comprised improved alertness, cognition with quicker response; improved memory function, particularly for recall of recent events; improved numerical calculation; reduction of drowsiness and dizziness; reduction of anxiety and depression; and increased energy and vitality. Additionally, the patients treated with the herbal extract-based composition according to the present invention showed a statistically significant reduction in body weight of 1.41 kg±0.56 (standard deviation; $P<0.05$); a statistically significant reduction of abdominal circumference of 1.76 cm±0.56 ($P<0.01$); a decreased blood viscosity, a decrease in cholesterol of 20 mg±5 (standard deviation), a decrease in serum triglycerides of 28.6 mg±7.8, and a statistically significant decrease in fibrinogen of 88.6 mg±9.1 ($P<0.05$), as compared to the respective measurement before treatment was initiated.

EXAMPLE 3

In this embodiment is illustrated the use of the herbal extract-based composition of the present invention. In this illustration, treated with the caplet form (as described in Example 1) were six patients (mean age 56) suffering from transient ischemia attacks, cerebrovascular spasm, and several cases of multiple lacunar cerebral infarction with a long-standing history of hypertension. After treatment for at least 30 days, the patients showed improved general conditions including improved memory, increased mental awareness, decreased vertigo and dizziness, a reduction in fatigue, increased physical endurance and improved fine motor coordination, a reduction of facial muscular weakness, and a cessation of transient ischemia attacks. Additionally, the patients treated with the herbal extract-based composition according to the present invention showed a statistically significant reduction in body weight of 1.41 kg±0.56 (standard deviation; $P<0.05$); a statistically significant reduction of abdominal circumference of 1.76 cm±0.56 ($P<0.01$); a decreased blood viscosity, a decrease in cholesterol of 20 mg±5 (standard deviation), a decrease in serum triglycerides of 28.6 mg±7.8, and a statistically significant decrease in fibrinogen of 88.6 mg±9.1 ($P<0.05$), as compared to the respective measurement before treatment was initiated.

In another illustration of the health promoting effects by providing a reduction in fatigue, 1 group of mice was treated with the herbal extract-based composition according to the present invention using 60 mg/day (delivered by gastric tube) for 14 days. A control group of mice remained untreated. It is known that prolonged physical exertion, exercise, and prolonged mental concentration can generate an excess of lactate within the body; and that lactate release is a major cause of muscle fatigue (see, e.g., Hogan et al., *J. Appl. Physiol.* 65:815). As shown in Table 1, it was found treating mice with the herbal extract-based composition of the present invention (denoted "HEBC"), followed by an forced exercise regimen for seven hours, can speed up body metabolism for the elimination of lactate (43% reduction in serum lactic acid levels), as compared to the control group of mice (denoted "control"). Hence, in the treated group is a more rapid recovery from fatigue, resulting in increased physical and mental endurance as compared to the controls.

TABLE 1

| mice | Lactic acid (mg) before exercise | Lactic acid (mg) after exercise |
| --- | --- | --- |
| control | 250.0 ± 40.4 | 712.5 ± 25.3 |
| HEBC-treated | 250.0 ± 40.0 | 425.6 ± 65.2 |

In a further illustration of health promoting effects of the herbal extract-based composition according to the present invention, the composition was tested for anti-stress activity (effecting increased physical endurance) using the "mice swimming endurance test" (Grandhi et al., 1994, *J. Ethanopharmacol.* 44:131). A control group of 15 mice, a group of 15 mice treated with the herbal extract-based composition at a dosage of 60 mg/day for 14 days ("group 2"), and a group of 15 mice treated with the herbal extract-based composition at a dosage of 120 mg/day for 14 days ("group 3") were evaluated for swimming time in this assay. As shown in Table 2, a statistically significant increase in swimming time was shown in the mice treated with the herbal extract-based composition (groups 2 and 3; P<0.05) as compared to the control group.

TABLE 2

| mice | swim time (minutes) ± std. dev. |
|---|---|
| control | 13.79 ± 7.85 |
| group 2 | 22.85 ± 11.08 |
| group 3 | 24.68 ± 13.49 |

EXAMPLE 4

In this embodiment is illustrated the use of the herbal extract-based composition of the present invention. In this illustration, treated with the caplet form (as described in Example 1) were 80 obese patients and patients with hyperlipidemia. After treatment for at least 30 days, the patients showed an average reduction of body weight of 2.0 kg and a reduction in the levels of both serum triglyceride and cholesterol of 20%, as compared to pre-treatment measurements. Additionally, there was increased vitality, a sense of well-being, and improved skin appearance among the treated patients. For male patients, there was a reduction in the urinary frequency and nocturia, with palpable reduction of prostate size.

Improvement in skin appearance, as observed by a reduction and disappearance of acne, was also observed in a study of young individuals suffering from acne. Treatment of such individuals with the herbal extract-based composition according to the present invention was effective in reducing acne with a treatment period of at least 30 days. Other benefits to the skin observed in individuals using the herbal extract-based composition include a decreased pigmentation of senile freckles. In another illustration of health promoting effects provided by the herbal extract-based composition according to the present invention, the composition was tested for its ability to reduce malondialdehyde (MDA) in the serum of treated animals. A known breakdown product of lipid peroxides in aging skin is MDA. MDA has been shown to cross-link with collagen, which is one mechanism by which the elasticity of skin decreases with age. A control group of 10 mice, and a group of 10 mice treated with the herbal extract-based composition (by gastric tube—60 mg/day for 14 days; group 2) were evaluated for the ability to reduce the formation of MDA. As shown in Table 3, group 2 demonstrated a statistically significant decrease in MDA as compared to the control group.

TABLE 3

| mice | MDA μmol/ml ± std. dev. | % change from control |
|---|---|---|
| control | 1.201 ± 0.12 | — |
| group 2 | 0.923 ± 0.15 | −20.2 |

EXAMPLE 5

In this embodiment, the health promoting effects of the herbal extract-based composition according to the present invention are further illustrated. Ten patients (mean age 56±4.3; 7 males, 3 females) with severe coronary atherosclerosis and varying degrees of myocardial ischemia began taking the caplet form (as described in Example 1) for at least 30 days. Following the treatment period, the patients showed reductions in frequencies and intensities of angina and tachycardia, decreased anxiety and depression, an improved sense of well being, improved EKG tracings with decreased arrhythmia, and decreases in serum cholesterol levels (15 mg/dl±4) and triglyceride levels (50 mg/dl±8.4), and a decrease in the level of plasma fibrinogen (150 mg/dl±21).

EXAMPLE 6

In this embodiment, the health promoting effects of the herbal extract-based composition according to the present invention are further illustrated. Radiation (e.g., $^{60}$Cobalt) can induce cytogenic damage in leukocytes resulting in more leukocytes with micronuclei in the peripheral circulation. Thus, peripheral leukocytes with micronuclei in individuals may be used as an index to cytogenic damage induced by radiation exposure. Sixty patients (30 male, 30 female, mean age 52 years) with an advanced stage of a malignant tumor received standard radiation therapy. In 97% of the patients receiving the herbal extract-based composition according to the present invention (caplet form, as described in Example 1), leukopenia was reduced (e.g., by as much as about 50%) following radiation therapy.

To further illustrate the protection of leukocytes from radiation damage and killing, a control group of 10 mice were untreated and not exposed to radiation. A second group of control mice were untreated and then exposed to a standard dose (300 rads) of $^{60}$Co (group 2). A third group of mice was treated with 300 mg/kg of body weight/day of the herbal extract-based composition according to the present invention (by gastric tube, and for 10 days), and exposed to a standard dose of $^{60}$Co (group 3). A fourth group of mice was treated with 400 mg/kg of body weight/day of the herbal extract-based composition according to the present invention (by gastric tube, and for 10 days), and exposed to a standard dose of $^{60}$Co (group 4). As shown in Table 4, there were statistically significant reductions in micro-nucleus formation and leukopenia (as measured by the number of white blood cells/mm) in the mice treated with the herbal extract-based composition as compared to group 2 (untreated, irradiated).

TABLE 4

| mice | WBC/mm ± std. dev. | Change (%) | Micronucleus (%) |
|---|---|---|---|
| control | 7000 ± 550 | — | 2.3 |
| group 2 | 1910 ± 450 | −72.7 | 17.6 |
| group 3 | 4110 ± 4331 | +115.2 | 4.0 |
| group 4 | 4500 ± 4701 | +135.2 | 2.1 |

From the foregoing, it will be obvious to those skilled in the art that various modifications in the above-described methods, and compositions can be made without departing from the spirit and scope of the invention. Accordingly, the invention may be embodied in other specific forms without departing from the spirit or essential characteristics thereof. Present embodiments and examples, therefore, are to be considered in all respects as illustrative and not restrictive, and all changes which come within the meaning and range of equivalency of the claims are therefore intended to be embraced therein.

What is claimed is:

1. An herbal based composition comprising, as components, about 10 to 30 percent by weight of a mixture of an aqueous extract and an alcohol extract of *Gynostemma pentaphyllum,* about 40 to about 75 percent by weight of a mixture of an aqueous extract and an alcohol extract of *Crataegus pinnatifida* (hawthorn berries), and about 10 to about 30 percent by weight of a mixture of an aqueous extract and an alcohol extract of *Camellia sinensis* (green tea).

2. The herbal based composition according to claim 1, wherein the herbal based composition comprises about 20 percent by weight of said *Gynostemma pentaphyllum* extract, about 20 percent by weight of said *Camellia sinensis* extract, and about 60 percent by weight of said *Crataegus pinnatifida* extract.

3. The herbal based composition according to claim 1, further comprising a gum base for forming a chewing gum.

4. The herbal based composition according to claim 3, wherein the gum base is selected from the group consisting of arabic, guar, and natural rubber gum.

5. The herbal based composition according to claim 4 further comprising a sweetener, flavoring agent, coloring agent, or a combination thereof.

6. The herbal based composition according to claim 1, further comprising an aqueous carrier.

7. The herbal based composition according to claim 3, wherein the aqueous carrier is selected from the group consisting of spring water, filtered water, distilled water, carbonated water, juices, and a combination thereof.

8. The herbal based composition according to claim 7, further comprising a component selected from the group consisting of a preservative agent, sweetener, flavoring agent, coloring agent, and a combination thereof.

9. The herbal based composition according to claim 1, further comprising a cream or ointment base for topical application.

10. The herbal extract-based composition according to claim 9, wherein the cream or ointment base is selected from the group consisting of lanolin, propylene glycol, mineral oil, vegetable oils, flower oils, glycerin, glyceryl stearate, and propylparaben.

11. The herbal based composition according to claim 10 further comprising preservatives, fragrances, or a combination thereof.

12. The herbal based composition according to claim 1, further comprising a tablet base for forming a tablet formulation.

13. The herbal based composition according to claim 12; wherein the tablet base is selected from the, group consisting of a filler, binder, coating, excipient, and a combination thereof.

14. The herbal based composition according to claim 12, wherein the tablet base is selected from the group consisting of plant cellulose, natural silica, magnesium stearate, wax, vegetable glycerides, vegetable stearate, and a combination thereof.

15. A process for preparing the herbal based composition of claim 1, comprising the steps of:

(a) separately extracting a first batch of each of three herbal components, wherein the components are macerated *Crataegus pinnatifida*, cut *Camellia sinensis* leaves, and cut *Gynostemma pentaphyllum* leaves, in water at least at room temperature for at least one hour, wherein the ratio of each herbal component to water is about 5:1;

(b) recovering separately a first extraction eluate from the respective extraction of each herbal component;

(c) re-extracting separately each herbal component by repeating step (a), recovering separately a second extraction eluate, and pooling the second extraction eluate with the first extraction eluate of the respective herbal component;

(d) separately extracting a second batch of each of three herbal components, wherein the components are macerated *Crataegus pinnatifida*, cut *Camellia sinensis* leaves, and cut *Gynostemma pentaphyllum* leaves, in an aqueous alcohol at room temperature for at least one hour, wherein the ratio of aqueous alcohol to each herbal component is about 5:1;

(e) recovering separately a first aqueous alcohol extraction eluate from the respective extraction of each herbal component in the second batch;

(f) re-extracting separately the second batch of each herbal component by repeating step (d), recovering separately a second aqueous alcohol extraction eluate, and pooling the second aqueous alcohol extraction eluate with the first aqueous alcohol extraction eluate of the respective herbal component;

(g) recovering an organic residue from each of the pooled extraction eluates by reducing the liquid portion of each of the pooled extraction eluates by drying to produce a dried residue, combining the dried residues from the first and second batch for each component to form a *Camellia sinensis* extract powder, a *Gynostemma pentaphyllum* extract powder, and a *Crataegus pinnatifida* extract powder; and (h) combining the *Camellia sinensis* extract powder, the *Gynostemma pentaphyllum* extract powder, and the *Crataegus pinnatifida* extract powder to form the herbal based composition.

16. The process according to claim 15, wherein the water of step (a) is in a temperature range of from 70° C. to 80° C.

17. The process according to claim 16, wherein the water is in contact with each herbal component for a time in a range of 2 to 4 hours.

18. The process according to claim 15, wherein the aqueous alcohol is 70% ethanol at room temperature.

19. The process according to claim 15, wherein the drying in step (g) is a process selected from the group consisting of air drying, freeze-drying, and a combination thereof.

20. The process according to claim 15, wherein the aqueous alcohol is in contact with each herbal component for a time in a range of 2 to 4 hours.

* * * * *